United States Patent [19]

Daniel

[11] 4,439,621

[45] Mar. 27, 1984

[54] OXYDEHYDROGENATION PROCESS

[75] Inventor: Chelliah Daniel, Columbus, Ohio

[73] Assignee: Ashland Oil, Inc., Ashland, Ky.

[21] Appl. No.: 404,206

[22] Filed: Aug. 2, 1982

[51] Int. Cl.³ .................. C07C 67/317; C07C 51/377
[52] U.S. Cl. .................................. 562/599; 560/214; 502/509
[58] Field of Search ....................... 560/214; 562/599; 568/459; 502/209

[56] References Cited

U.S. PATENT DOCUMENTS

| | | | |
|---|---|---|---|
| 4,249,020 | 2/1981 | McNeil et al. | 560/214 |
| 4,331,813 | 5/1982 | Daniel et al. | 560/205 |
| 4,370,490 | 1/1983 | Gruber et al. | 560/214 |

*Primary Examiner*—Natalie Trousof
*Assistant Examiner*—L. Hendriksen
*Attorney, Agent, or Firm*—John F. Jones

[57] ABSTRACT

Isobutyric acid or a lower alkyl ester thereof is oxidatively dehydrogenated in the vapor phase producing the corresponding olefinically unsaturated derivative by contact with a heterogeneous catalyst in the presence of molecular oxygen. The catalyst is composed of the calcined oxides of iron, phosphorous, silicon, vandanium and molybdenum.

3 Claims, No Drawings

OXYDEHYDROGENATION PROCESS

BACKGROUND OF THE INVENTION

1. Field of the Invention

This invention relates to the conversion of isobutyric acid or its equivalents and lower alkyl esters thereof correspondingly to methacrylic acid or its equivalents and lower alkyl esters thereof.

2. Description of the Prior Art

There exists considerable prior art relating to the oxydehydrogenation of the lower saturated aliphatic monocarboxylic acids to produce the corresponding alpha, beta-olefinically unsaturated acids. Early work in this area involved thermal, vapor phase oxydehydrogenation of the saturated aliphatic carboxylic acid in the presence of oxygen and iodine. This approach has not been particularly successful from a commercial standpoint. This is understandably so inasmuch as iodine is costly, exhibits extreme corrosion properties and poses considerable problems in realizing complete recovery of the comparatively large amounts thereof required in the process. The heterogeneous catalytic method of oxydehydrogenation according to the prior art appears to be the more attractive route to the commercial production of alpha, beta-olefinically unsaturated monocarboxylic acids. The prior art heterogeneous oxydehydrogenation catalysts useful for this purpose include some heteropoly acids, such as phosphomolybdic acid, optionally with tungsten and/or vanadium (U.S. Pat. No. 4,061,673). Another type of prior art catalyst useful in the oxydehydrogenation of aliphatic carboxylic acids and esters thereof is iron phosphate.

Iron phosphate subjected to calcination exists in several crystalline phases or species. It is not known at this time which species is or are catalytically active. There is evidence that the presence of certain extrinsic metal components in the catalyst preparation serves to facilitate the formation of an active catalyst. U.S. Pat. No. 3,948,959, for instance, discloses that an alkali or alkaline earth metal can be the extrinsic metal for this purpose. In general, oxydehydrogenation catalysts of the type discussed above function best when relatively large quantities of steam are included in the feed along with the carboxylic acid and molecular oxygen. The prior art catalysts also usually work best at relatively higher temperatures. In contrast, the catalysts embodied in the process of my invention work best at relatively lower reaction temperatures with relatively lower amounts of steam in the reactor feed.

SUMMARY OF THE INVENTION

In accordance with this invention, a catalytic process is provided for the oxidative dehydrogenation of a saturated aliphatic monocarboxylic acid or lower alkyl thereof, such as isobutyric acid or methyl isobutyrate, to the corresponding alpha, beta-olefinically unsaturated derivative, such as methacrylic acid or methyl methacrylate. The process of this invention comprises contacting a heterogeneous catalyst at a temperature in the range of from about 260° to 450° C. with a mixture of the saturated aliphatic monocarboxylic acid and molecular oxygen, said catalyst being a calcined oxide of iron, phosphorous, silicon, vanadium and molybdenum. The catalyst useful in this invention can be further defined by the gram-atom emperical formula $Fe_aP_bSi_cV_dMo_eO_x$ wherein a is 0.05–1.0, b is 0.05–2.0, c is 0.05–2.0, d is 0.5–6.0, e is 6–12.0 and x represents the number of oxygens required to satisfy the uncombined positive valences of the other elements shown in the formula.

DESCRIPTION OF THE PREFERRED EMBODIMENT

There are a number of techniques for preparing the catalysts useful in the process of the invention. Of these, the more facile methods involve preparing the integral catalyst composition prior to calcination. This can be done by the so-called slurry method or the precipitation method. In the latter method an aqueous solution of salts of the metals and phosphoric and silicic acid is first prepared and is then neutralized with an appropriate base so as to precipitate the mixed metal oxide silico phosphomolybdates. The precipitate is usually washed and dried prior to calcination. In the alternative, one can add ammonium phosphate, ammonium silicate, and ammonium molybdate to a solution of the metal salts causing direct precipitation of the metal oxides and heteropoly acids salts. As indicated, any water-soluble salt or iron, vanadium and molybdenum can be used in the preparation of the solution. The nitrate salts are suitable water-soluble salts for this purpose and are preferred because of their ready availability and desirable solubility characteristics.

The so-called slurry method is the preferred catalyst preparation method because of its convenience. In accordance with this procedure the aqueous solution of the metal salts and acids of the other elements is obtained as previously noted. The solution is then heated with stirring to remove water and this is continued until the mass is so thick it cannot be stirred. The resulting residue is then broken up and heated to a moderately elevated temperature on the order of about 120° C. until the mass is completely dried. The resulting solid is sized and calcined in air. Suitable calcination temperatures range from 300°–500° C. Applicable periods of calcination range from 2–30 hours or more.

The use of a support or carrier for the catalyst is included in this invention. The support can be included in either of the catalyst preparation methods mentioned above. For instance, in the slurry method colloidal silica or any other form of silica as well as other support material such as alumina, quartz, titanium dioxide, carbon, silicon carbide, etc., can be included prior to the water removal step. Similarly, the precipitation of the catalyst can be accomplished in the presence of suspended particles of the support material in the alternate method described above.

The process of this invention can be carried out using the catalyst in the form of a fluidized bed reactor, a stirred tank reactor or in a fixed bed or packed bed reactor or any combination of these types of reactor configurations. Because of the convenience associated with the use of a fixed bed reactor in a small scale operation, such a reactor will be exemplified herein. In the preferred mode of operation the feed to the reactor comprises a pre-heated gaseous mixture of the saturated aliphatic monocarboxylic acid, molecular oxygen, steam and inert gas. A pre-heat temperature in the range of about 250° to 350° C. is customarily used. The oxydehydrogenation reaction can be carried out in the range of from about 260° to 450° C. More generally, a temperature of from about 280° to 320° provides for optimum processing.

The mole ratio of molecular oxygen to carboxylic acid is from 0.5 to 1.5 and more preferably from 0.7 to 0.75 in the case in which the carboxylic acid is isobutyric acid. Although steam is not necessary for the reaction, its presence is desirable in the feed because it is believed to act beneficially as a heat sink and in minimizing combustion of the carboxylic acid to undesirable waste products. The mole ratio of water to the carboxylic acid in the feed should be from 0.1 to 20. The preferred ratio is from 1 to 5.

Another important parameter is the concentration of the organic acid or ester reactant in the feed. The organic reactant carboxylic acid or ester should be present in the feed in from 0.1 to 20 mole percent.

From the standpoint of achieving a reasonable throughput combined with an acceptable yield, the concentration of the organic reactant in the feed is from about 3-16 mole percent. Concentration of the organic reactant in the feed is controlled to a large degree by the amount of inert gas present. The preferred inert gas or diluent is nitrogen although other inert gases such as carbon dioxide, helium, argon, and the like are suitable. Air is a very convenient source of oxygen plus inert diluent.

Another important parameter is contact time in the process of this invention. Contact time is defined for the purpose of this invention as the catalyst volume divided by the volume of gas feed per second at the reaction temperature. The catalyst volume is the bulk volume occupied by the catalyst in the reactor. The term "catalyst" in this sense not only includes the active components of the catalyst as defined by the empirical formula given above but also includes the support if present. Accordingly, reaction times can range from 0.05 to 3.0 seconds and more specifically in the order of from 0.1 to 1.0 seconds. The reaction is preferably carried out at or near atmospheric pressure although the use of higher pressures up to about 10 atmospheres is contemplated.

The process of this invention is further illustrated in the following specific examples.

EXAMPLE 1

This example illustrates the use of the slurry method for preparation of the catalyst on a silica carrier. A slurry was made by combining 400 ml of water, 213.2 g of ammonium molybdate, 16.01 g of ammonium vanadate, 11.022 g of silicic acid and 8.0 ml of 85% phosphoric acid. It is mixed with 150 ml Ludox 40 HS (a 40% aqueous silica sol, DuPont) and 80.0 grams of ferric nitrate. The slurry was stirred and volatiles were removed with heat. The residue was broken up and calcined at 320° for 15 hours in air. The final composition was found by analysis to have the composition $Fe_2P_{1.2}Si_1V_1Mo_{12}O_x/SiO_2 25\%$.

EXAMPLE 2

This example illustrates the use of the catalyst described in Example 1 in the oxydehydrogenation of isobutyric acid to produce methacrylic acid. The procedure consisted of feeding a pre-heated mixture of isobutyric acid, oxygen, nitrogen and steam through a stainless steel tube of $\frac{1}{2}''$ O.D., $\frac{3}{8}''$ i.d. and approximately 18" in length containing the catalyst as a 15 cc packed bed maintained at the reaction temperature of 314° C. The preheater consisted of a length of stainless steel tubing similar to the reactor but packed with glass beads. Any carbon dioxide formed in the course of the reaction was absorbed in an Ascarite absorber protected by a calcium sulfate absorber for any uncondensed water. The condensed organic product was separated from the water, collected and analyzed by the internal standard method of gas chromatography.

Selectivity to methacrylic acid represents the mole ratio of methacrylic acid found in the reaction effluent to that of the isobutyric acid consumed in the reaction.

The feed to the reactor was composed of isobutyric acid:oxygen:water:nitrogen in the corresponding mole ratio of 3.2:3.8:4.6:88.2. The contact time was 0.55 sec. 80.5% of the isobutyric acid in the feed was converted with a selectivity to methacrylic acid of 73.74%.

EXAMPLE 3

The procedure of Example 2 was repeated except that the reaction temperature was increased to 323° C. and the feed was composed of isobutyric acid:oxygen:water:nitrogen in the corresponding mole ratio of 3.4:3.3:17.2:76. The contact time was 0.50 sec. 86.8% of the isobutyric acid was converted with a selectivity to methacrylic acid of 67.1%.

I claim:

1. In a process for the catalytic conversion of isobutyric acid or ester to the corresponding alpha, beta-olefinically unsaturated derivative by oxydehydrogenation wherein a catalyst is contacted with a gaseous stream containing said acid or ester and molecular oxygen at an elevated temperature; the improvement comprising carrying out the process at a temperature in the range of from 260° to 450° C. using as catalyst a material having the gram-atom emperical formula $Fe_aP_bSi_cV_dMo_eO_x$ wherein a is 0.05-1.0, b is 0.05-2.0, c is 0.05-2.0, d is 0.5-6.0, e is 6-12.0, and x is a number that satisfies the sum of the unshared positive valences of the other elements shown in the formula.

2. The process of claim 1 where isobutyric acid is converted to methacrylic acid.

3. The process of claim 2 wherein the catalyst has the gram-atom emperical formula $Fe_2P_2Si_1V_1Mo_{12}O_x/SiO_2 25\%$.

* * * * *